(12) United States Patent
Rao et al.

(10) Patent No.: US 7,212,607 B1
(45) Date of Patent: May 1, 2007

(54) X-RAY CONFOCAL DEFECT DETECTION SYSTEMS AND METHODS

(75) Inventors: Satyavolu Srinivas Papa Rao, Garland, TX (US); Richard L. Guldi, Dallas, TX (US); Basab Chatterjee, Allen, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 11/346,054

(22) Filed: Feb. 2, 2006

(51) Int. Cl.
*G01B 15/06* (2006.01)

(52) U.S. Cl. ........................................... 378/58

(58) Field of Classification Search ............ 378/51, 378/57, 58, 62, 145, 147; 250/370.01, 370.08, 250/370.09
See application file for complete search history.

(56) References Cited

U.S. PATENT DOCUMENTS 4,736,397 A * 4/1988 Velasquez ................ 378/98.3
6,488,037 B1 12/2002 Guldi ........................ 131/1.3
6,834,117 B1 12/2004 Rao et al. .................. 382/149

* cited by examiner

*Primary Examiner*—Courtney Thomas
(74) *Attorney, Agent, or Firm*—Peter K. McLarty; W. James Brady, III; Frederick J. Telecky, Jr.

(57) ABSTRACT

An x-ray confocal defect detection system comprises an x-ray source, a confocal component, and defect detectors and operates on a target portion of a semiconductor device. The x-ray source generates x-ray energy. The semiconductor device includes a plurality of formed layers. The target portion is a selected layer or portion of the plurality of formed layers. At least a portion of the x-ray is transmitted through the semiconductor device as transmitted x-ray. The confocal component receives the transmitted x-ray and passes target x-ray intensity from the target portion of the transmitted x-ray energy. Detectors receive the target x-ray from the confocal component from which defect analysis can be performed.

24 Claims, 4 Drawing Sheets

X-RAY CONFOCAL DEFECT DETECTION SYSTEMS AND METHODS

FIELD OF INVENTION

The present invention relates generally to semiconductor devices and more particularly to x-ray defect detection.

BACKGROUND OF THE INVENTION

Semiconductor fabrication faces shrinking device dimensions and increasing process complexity. Devices of today are smaller and require more fabrication processes than devices of even a few years ago. Additionally, the shrinking dimensions require ever tighter tolerances for performance of the process employed in semiconductor fabrication.

Semiconductor manufacturers generally recoup their manufacturing costs by selling their fabricated semiconductor devices. However, some semiconductor devices fail to meet operational requirements and are, therefore, unable to be sold. As a result, the manufacture does not recoup the manufacturing costs for the failed devices.

A critical statistic in semiconductor fabrication is yield, which is a percentage of devices fabricated that meet operational requirements. A goal of device fabrication process is to reach 100 percent yield, although this goal is not generally obtained. However, the closer to this goal and the higher the yield, the greater the profitability for the manufacturer.

Semiconductor fabrication processes and the devices themselves are very sensitive to out of tolerance process conditions, mishandling, movement, temperature, humidity, and the like. As a result, defects in structures and layers present in semiconductor devices can occur.

An important step in the manufacture of integrated circuits is the formation of metal conductors, which provide electrical connections to devices formed therein. Conductors in integrated circuits are typically formed of copper metallization, in order to take advantage of the lower resistance of copper (though aluminum is also used in certain cases). The minimum line width is sought to be minimized, since it is often a factor upon which the overall integrated circuit chip area depends. In order to minimize the chip area required for realization of complex integrated circuits such as digital signal processors (DSPs) or microprocessors, multiple metallization levels are common in the art, despite the complex manufacturing processing required for their fabrication.

Voiding in metal conductors is an important defect that can occur in the fabrication of thin, closely-spaced, metal conductors, particularly in multiple layers. Voids may be caused in the deposition of the metal film, as a result of metal etch, or by unintended corrosion during processing. Voids can also be caused by migration of atoms during thermal processing under stress fields that develop over the metal line, or due to electrical currents; voids in metal conductors can also be present because of the inability of large grains to fill gaps, particularly in small geometries and over topography. Because of the yield loss due to defective metal lines, and also considering later-life reliability hazards resulting from the void, the prevention and/or mitigation of voids in metal conductors is important in modern integrated circuit manufacturing.

In previous years with larger devices, metal voids could be readily detected by optical inspection (automated or otherwise) of the integrated circuits during or after their manufacture. Additionally, the reduction in metal conductors to the sub-micron range has not only reduced the optical visibility of the conductors, but also reduced the minimum size of a killing void further below the visibility of optical microscopy. In addition, the presence of voids within the body of a conductor line generally cannot be detected by visual or scanning electron microscopy (SEM) techniques that are currently in use. Particularly in damascene copper structures, voids are sometimes buried, and are thus optically invisible, regardless of the conductor dimensions. The implementation of multiple metal levels has also limited optical inspection, because the 'noise' introduced by the grains in the underlying metal level reduces the efficacy of automated inspection of the top-most metal at any particular point in the fabrication sequence.

As a result, at least some conventional void detection relies upon destructive techniques. Typically, sample wafers from the manufacturing line are cross-sectioned, and the cross-sections are examined by SEM for a measure of the metal film quality. The destructive nature of this inspection reduces the number of samples that may be inspected by SEM. Furthermore, the nature of SEM precludes the viewing of more than a small number of locations of the wafer within each sample. The preparation of the cross-sectional samples for SEM analysis is also time-consuming, and thus costly. As such, routine SEM inspection is not a very effective, feasible measure of the metallization film quality.

Some other techniques are currently being developed for measuring the quality of metallization films. Magnetic force microscopy measures variations in magnetic flux caused by voids in the metallization; of course, this measurement not only requires current to be conducted through the conductor during measurement, but also highly precise magnetic field detection elements. Surface acoustic wave (SAW) microscopy has also been proposed, in which variations in reflection of acoustic waves due to voids may be measured, but resolution considerations tend to limit the applicability of SAW microscopy to small geometries. Additionally, some of the proposed methods utilizing SAW microscopy essentially rely upon 'golden' structures that are void-free but otherwise identical to the conductor structure being inspected, which is an onerous stipulation.

SUMMARY OF THE INVENTION

The following presents a simplified summary in order to provide a basic understanding of one or more aspects of the invention. This summary is not an extensive overview of the invention, and is neither intended to identify key or critical elements of the invention, nor to delineate the scope thereof. Rather, the primary purpose of the summary is to present some concepts of the invention in a simplified form as a prelude to the more detailed description that is presented later.

The present invention facilitates defect detection by employing x-ray analysis and a relatively narrow depth of field. As a result, single layers, such as a single metallization layer, can be examined without surrounding layers interfering with the analysis. The present invention obtains the narrow depth of field by employing a confocal mechanism that blocks contrast information carried by x-ray energy from other portions within the sample and passes only the contrast information carried by x-ray energy from a selected or targeted portion of a semiconductor device. Thereafter, defect detection is performed on the x-ray image from the targeted portion without interference from other portions of the sample.

In accordance with an aspect of the present invention, an x-ray confocal defect detection system comprises an x-ray source, a confocal component, and defect detectors, and operates on a target portion of a semiconductor device. The x-ray source generates x-ray energy. The semiconductor device includes a plurality of formed layers. The target portion is a selected layer or portion of the plurality of formed layers. At least a portion of the x-ray energy or intensity is transmitted through the semiconductor device as transmitted x-ray energy. The confocal component receives the transmitted x-ray energy and passes target x-ray image from the target portion of the sample through the transmitted x-ray energy. The confocal component comprises a first focus component, such as a lens or zone plate, a confocal aperture plate, and a second focus component, such as a lens or zone plate. The confocal aperture plate comprises an aperture through which the target image passes while images from other portions is blocked. Detectors receive only the target x-ray image from the confocal component from which defect analysis can be performed. This selection of the target layer is achieved by physically placing the first focus component in between the wafer and the confocal aperture plate such that the target layer of the sample is focused at the confocal aperture plate. Other portions of the wafer are in focus either before the confocal aperture plate's position or after it. As a result, the contrast information (image) from these portions is blocked by the confocal aperture plate, while the contrast information (image) from the target portion passes through the hole (aperture) in the confocal aperture plate. This image that passes through the hole is imaged onto the detectors by the second focus component.

In accordance with another aspect of the present invention, a method for identifying defects is provided. A wafer for defect detection is provided and a target layer of the wafer is selected for analysis. X-ray energy is then generated and passes through the wafer, including the selected layer. X-ray energy carrying the target image alone is transmitted through the aperture of the confocal aperture plate in the manner described above. The target x-ray energy is again focused toward a second focal point and is then received by detectors, which comprise an array of x-ray detectors. The detectors are then employed to analyze the target x-ray energy and identify defects.

The following description and annexed drawings set forth in detail certain illustrative aspects and implementations of the invention. These are indicative of but a few of the various ways in which the principles of the invention may be employed.

DETAILED DESCRIPTION OF THE INVENTION

One or more implementations of the present invention will now be described with reference to the attached drawings, wherein like reference numerals are used to refer to like elements throughout, and wherein the illustrated structures are not necessarily drawn to scale.

The present invention facilitates defect detection by employing x-ray analysis and a relatively narrow depth of field. As a result, single layers, such as a single metallization layer, can be examined without surrounding layers interfering with the analysis. The present invention obtains the narrow depth of field by employing a confocal mechanism that blocks planes of x-ray energy from other portions and passes x-ray energy from a selected or targeted portion of a semiconductor device. Thereafter, defect detection is performed on the targeted x-ray energy without interference from other x-ray energy.

Figure 1:
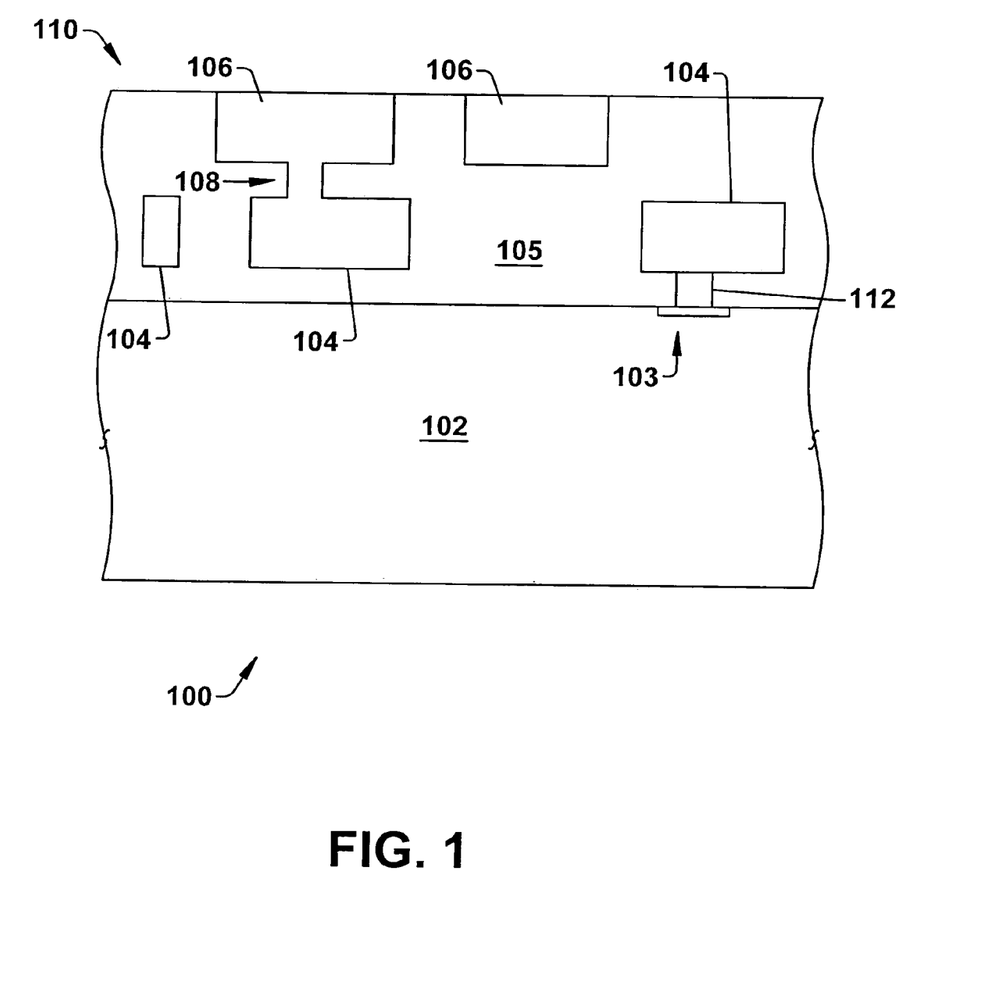
FIG. 1 is a cross sectional view of an exemplary semiconductor device having metallization layers.

FIG. 1 is a cross sectional view of an exemplary semiconductor device 100 having metallization layers. The device 100 is presented and described in order to facilitate understanding of the present invention.

The device 100 includes a semiconductor body 102 wherein discrete devices, layers, structures, and the like are formed. An exemplary source/drain region 103 is shown to further illustrate the device 100. A metallization structure 110 is formed on the semiconductor body 102 and provides electrical connection to the devices and structures formed therein, including the source/drain region 103.

The metallization structure 110 comprises a first copper layer 104 and a second copper layer 106, arranged in multiple levels near its top surface and insulated from one another by a dielectric material 105. The second copper layer 106 is formed above the first copper layer 104 and can be referred to as an upper conductive layer.

A copper plug 108 is shown that connects the second copper layer 106 to the first copper layer 104 at the selected location. Additionally, the first copper layer 104 and the second copper layer 106 can make contact with underlying circuitry structures, such as the source/drain region 103, using tungsten plugs 112. As shown in FIG. 1, the first copper layer 104 is in contact with the source/drain region 103.

An exemplary technique for the fabrication of multiple levels of copper layers/conductors is referred to in the art as the "damascene" process, in which the copper 104 and 106 are effectively inlaid into slots or tracks etched into an insulator layer (or multilayer dielectric film). According to this process, a relatively thin layer of copper is initially deposited over the etched dielectric material (and possibly over an adhesion and diffusion-barrier layer of a refractory metal compound), to serve as a seed layer. The remainder of the copper metallization layer, which will generally be the large majority of the thickness of the copper film, is then electroplated overall. Chemical-mechanical polishing (CMP) of the wafer levels off the electroplated copper layer to the top surface of the insulator layer, inlaying the copper layers 104 and 106 at the desired locations. Additional insulating layers and copper conductive levels are then formed as desired, for example by way of additional iterations of the damascene process. Vias through the dielectric may be filled with copper, tungsten, or some other metal, to interconnect the copper layers 104 and 106 result in differing metallization levels, for example as shown by plug 108 of FIG. 1.

After metallization specified by the design of the overall integrated circuit, wafer fabrication will generally be completed by the application of a protective overcoat, through which openings to metal bond pads or other connective lands are made. Following wafer fabrication and any desired electrical testing of the integrated circuits in wafer form, such "back-end" processes as dicing of the individual circuits from the wafer, electrical test, packaging, burn-in, and additional electrical testing, are then typically performed to result in a packaged integrated circuit that may then be implemented into end equipment.

The arrangement illustrated in FIG. 1 is provided for illustrative purposes and is not drawn to scale. According to modern integrated circuit fabrication technologies, the thickness of the copper layers 104 and 106 is, for example, typically in the range of about 0.05–1.5 micro-meters (e.g., formed into a 0.05–1.5 micro-meters trench in dielectric 105). Also according to some current technologies, a minimum width of the copper layers 104 and 106 may be less than 0.1 micro-meters. On the contrary, wafer thickness may be on the order of 600 to 725 micro-meters for wafers of conventional diameter such as 200 mm and larger.

It is noted that defects can result in formed layers of semiconductor devices, such as the device 100 of FIG. 1. The defects can include, for example, metal voids, seams, residue, remaining barrier metal, and the like. Additionally, the defects can also include defects or voids within other types of semiconductor layers, such as dielectric layers. Conventional defect detection mechanisms have a relatively high depth of field and can be unable to accurately analyze individual layers for defects. Furthermore, newer types of dielectric materials, such as low-k dielectrics, that may be employed make defect detection more difficult because of their lower density. The present invention can detect the presence of relatively small (e.g., on the order of 0.1 .micro-meters diameter) voids in the copper layers 104 and 106 by employing a relatively narrow depth of field that allows analysis of individual layers and/or portions of individual layers without substantial interference from over and underlying layers.

Figure 2:
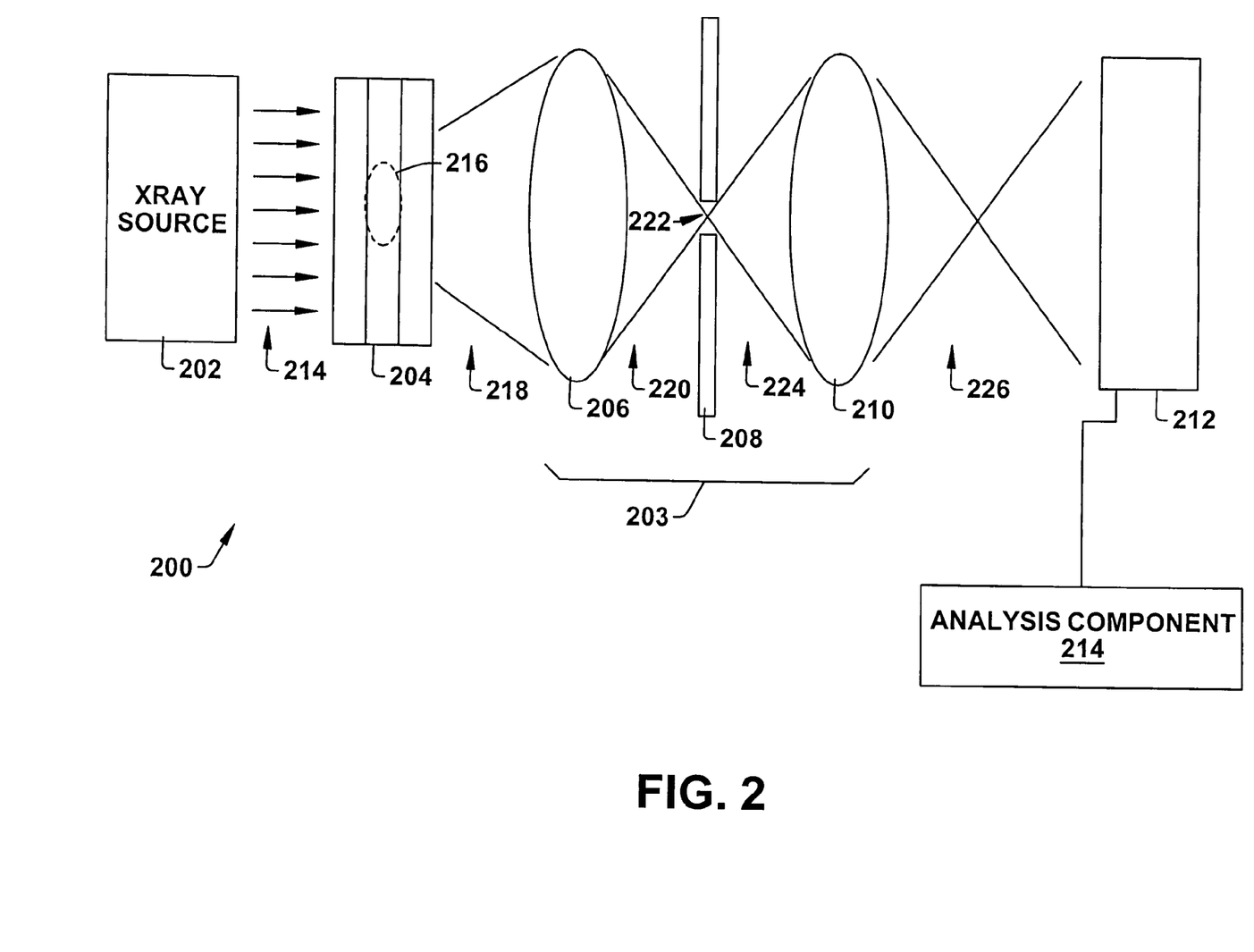
FIG. 2 is a diagram illustrating an x-ray confocal defect detection system in accordance with an aspect of the present invention.

FIG. 2 is a diagram illustrating an x-ray confocal defect detection system 200 in accordance with an aspect of the present invention. The system 200 includes a confocal component 203 which limits or narrows the depth of field. Accordingly, the system 200 can examine layers or portions of semiconductor devices with a limited and/or narrow depth of field. Therefore, other portions and/or layers of the device do not interfere with a current portion being examined. As a result, a current portion of a semiconductor device can be examined for defects with greater accuracy and improved defect identification than conventional defect detection systems. In particular, the system 200 is operable to detect undesired voids within copper layers or copper conductors.

The system 200 includes an x-ray source 202, the confocal component 203, and defect detectors 212 and operates on a target portion 216 of a semiconductor device 204. The x-ray source 202 generates x-ray energy 214 according to a selected intensity and wavelength, which are chosen according to the target portion 216, the semiconductor device 204, and types of defects that may possibly be detected. For example, the composition and thickness of the semiconductor device 204 is related to the intensity and wavelength employed for the x-ray energy 214. For example, semiconductor substrates absorb x-ray energy and thus, the thicker the substrate, the more intensity required.

Generally, x-ray intensity I that is transmitted through a medium of thickness x as a function of an incident x-ray intensity $I_O$ and the x-ray absorption coefficient of the medium as follows:

$$I=I_O\exp(-\mu x)$$

In order to distinguish the absence or presence of a portion of the material of a thickness $\Delta x$, one may consider a differential x-ray intensity $\Delta I$:

$$|\Delta I|=I_O\mu\exp(-\mu x)\Delta x$$

As such, the differential x-ray intensity $\Delta I$ increases with increasing absorption coefficient $\mu$, because a higher absorption of energy by a material will necessarily result in increased contrast between locations having and not having the material. Void detection, for example, is enhanced by a high x-ray absorption coefficient $\mu$. The absorption coefficient $\mu$ depends not only upon the density of the material, but also upon the x-ray energy itself. In particular, the absorption coefficient $\mu$ of x-ray energy at a given wavelength and for a given electron shell of the material, varies with the ratio of the binding energy and the photon energy raised to the power of (5/2). Additionally, the absorption coefficient $\mu$ also depends upon the wavelength of the x-ray energy.

It is noted by the inventors of the present invention that a relatively thick silicon substrate with copper conductors dictates certain tradeoffs in the selection of x-ray energy. Because a high x-ray absorption coefficient facilitates the detection of voids in copper conductors or layers, one would be led to select x-ray wavelength and energy ratios that maximize the absorption coefficient. However, the same factors of wavelength and energy ratio that maximized the absorption coefficient in copper will also maximize the x-ray absorption coefficient of silicon. Therefore, selection of energy and wavelength for the x-ray energy 214 generated by the x-ray source 202 accounts for differential absorption rates or coefficients of materials within the semiconductor device 204, the types of defects to be identified, and the target portion 216.

The semiconductor device 204 is exemplary in nature and can include a wide variety of individual devices and/or components. The device 204 can be, for example, a memory device, processor, logic device, and the like. The semiconductor device 204 can be at least a portion of a semiconductor die of a semiconductor wafer. The semiconductor device 204 typically includes a plurality of layers, such as multiple metallization layers.

The target portion 216 is a selected portion of the semiconductor device 204 that is targeted for analysis and/or defect detection. The target portion 216 is typically a portion of a particular layer of the device 204, such as one of the metallization layers, dielectric layers, and the like. However, the target portion 216 can include more than a single adjacent layer. Generally, at least the target portion 216 has x-ray energy 214 transmitted there through, which allows subsequent defect detection. Some of the x-ray beam 214 is absorbed by the semiconductor device 204 during operation. A portion of the beam 214 does pass through the semiconductor device 204 and is referred to as passed or transmitted x-ray beam 218.

The confocal component 203 receives the passed x-ray beam 218 and selectively removes/filters a substantial portion of the passed x-ray beam 218 that is not from or focused on the target portion 216. A portion of the x-ray beam 218 from the targeted portion is permitted to pass as target x-ray beam 226. As a result of the confocal component 203, the target x-ray beam does not substantially contain x-ray contrast information from portions focused on other areas of the semiconductor device 204. As such, interference from other portions of the semiconductor device 204 is mitigated.

The confocal component 203 includes a first focus mechanism 206, a confocal plate 208 with a confocal aperture 222, and a second focus mechanism 210. The first confocal component 203 receives the passed x-ray energy 218 and selectively focuses x-ray energy 220 such that a portion of the energy 218 from the target portion 216 is directed toward the confocal aperture 222 and other portions are not.

Generally, the confocal plate 208 is designed and/or selected such that the selected portion 218 passes through its aperture while other non-selected portions are blocked and/or absorbed by the confocal plate 208. In one example, the confocal plate 208 is relatively thin at least around the aperture, such as about 0.1 to 2 microns thick. However, it is appreciated that other thicknesses can be employed in accordance with aspects of the present invention. Additionally, the aperture of the confocal plate 208 is sized according to the selected portion 218. Generally, the larger the aperture, the greater the intensity and the depth of field, for example, covering multiple layers. Conversely, the smaller the aperture, the narrower the depth of field, for example, covering only a single layer.

The confocal plate 208 is comprised of a material that blocks and/or absorbs x-ray beams, such as, Tungsten, Platinum, Iridium, Tantalum, Gold, and the like. (higher atomic element materials permit more effective blocking for a given thickness). It is appreciated that the confocal plate 208 may be composite in character, having for instance a thick silicon or Aluminum backing plate that is mechanically strong and having a larger diameter aperture, but which bears a thinner film of the higher atomic element material with a smaller aperture that is centered on the aperture of the backing material.

The confocal plate 208 has the aperture 222 which allows x-rays carrying contrast information from the targeted portion 216 of the semiconductor device to pass there through. Other energy or planes of energy within the focused x-ray beam 222 are blocked by the plate 208. An example of this is described below. The non-blocked portion of the x-ray beam 220 that passes through the aperture 222 is referred to as selected x-ray beam 224.

The second focus mechanism 210 receives the selected x-ray beam 224 and focuses the beam 224 toward the defect detectors 212 as the target x-ray beam 226. The defect detectors 212 are located a selected distance downstream from the second focus mechanism and analyze the target x-ray beam 226 in order to identify defects, such as copper voids, dielectric voids, and the like within the target portion 216 of the semiconductor device 204.

The first focus mechanism 206 and the second focus mechanism 210 are comprised of a lens or a zone plate in order to properly focus the x-ray energy. Generally, a lens is a device for either concentrating or diverging energy, typically formed from a piece of shaped material (glass, in the case of optical energy, Beryllium or Aluminum in the case of x-rays). A suitable lens uses refraction to bend or focus incoming x-ray energy toward a selected target. A zone plate is another mechanism used to focus x-ray energy. However, unlike lenses, zone plates use diffraction to focus x-ray energy and are also referred to as Fresnel zone plates. A zone plate, in one example, comprises a set of radially symmetric rings referred to as Fresnel zones, which alternate between opaque and transparent. Energy hitting the zone plate will diffract around the opaque zones. The zones can be spaced so that the diffracted light constructively interferes at a desired focal point. Zone plates produce equivalent diffraction patterns whether the central disk is opaque or transparent.

The first focus mechanism 206 and the second focus mechanism 210 have focusing properties selected to appropriately focus the x-ray beam. Additionally, the first focus mechanism 206, the confocal plate 208, and the second focus mechanism are placed selected distances apart. The size of the aperture 222 determines the selectivity of the aperture.

The focusing properties and the selected distances cause the x-ray beam 220 to converge at a focal point at a center of the confocal aperture 222. The size of the aperture 222 is selected to limit the depth of field of the source x-ray energy to be from the target portion 216. Typically, the size of the aperture 222 is selected to yield a depth of field that includes a substantial portion of a target layer, such as a metallization layer, without including substantial portions of x-ray energy from over or underlying layers.

The defect detectors 212, also referred to as x-ray detectors, receive and analyze the target x-ray energy 226 received from the confocal module 203. The defect detectors 212 are typically arranged in an array of individual x-ray detectors. The defect detectors 212 are generally, but not necessarily, comprised of solid-state x-ray detectors, such as those constructed of lithium-drifted silicon, or of gallium arsenide or other III-V semiconductor devices that are x-ray sensitive. As illustrated in FIG. 2, one or more of the single x-ray detector of the detectors 212 receive the target x-ray energy 226.

The individual detectors are typically coupled to an analysis component 214, which is typically comprised of a computer, circuitry, or logic, to which signals corresponding to the detected x-ray energy are communicated. Generally, the analysis component 214 receives x-ray detection signals, such as digital signals, from the defect detectors 212 and identifies defects there from. For example, the analysis component 214 in conjunction with the defect detectors 212 can identify defects such as, but not limited to, metal voids, seams, residue, remaining barrier metal, dielectric layer defects, and the like.

The analysis component 214 can store digital signals corresponding to the x-ray energy detected by the detectors 212 to identify defects within the target location 216. Additionally, the device 204 can be moved by way of a wafer translation system (not shown), which laterally translates the device 204 to reposition the target location 216 on the device and permit imaging of other portions of the device 204. This allows scanning various sites of the device which can then be compared to facilitate defect identification. For example, similar structures should have similar x-ray images and variations there between may indicate defects. Further, the analysis component 214 can employ energy dispersive spectroscopy analysis, so as to exclude the effects of any fluorescent x-ray generation caused by the x-ray irradiated device 204 and to allow for multiple x-ray wavelengths.

The analysis component 214 compares an x-ray image with previous x-ray images in order to identify defects. For die-to-die comparisons, as an example, the analysis component 214 compares the x-ray image with previous images of same relative locations in a plurality of nearest neighbor dies. If the x-ray image differs from the two reference die, the current die is deemed defective. For cell-to-cell comparisons, as another example, the analysis component 214 compares the x-ray image with previous images of same relative locations in a plurality of neighboring cells. If the x-ray image differs from the two reference cells, the current cell is deemed defective.

A separate controller component (not shown) may also be present in order to control and/or adjust the confocal component 203, the x-ray source 202, and the detectors 212. For example, the controller component can adjust parameters in order to adjust the depth of field of the target portion 216 in order to select different layer(s) and/or portions of layer(s).

As one example, this may be accomplished by indexing the wafer or the confocal aperture using stepper motors or piezoelectric actuators to translate the aperture closer to or further away from the focus component 206. Such minute translations (of the order of 0.1 um) can bring successive planes of metallization into focus. Additionally, differently sized apertures can be pulled into place to increase the intensity of x-ray beam 226 at the expense of depth resolution.

Figure 3:
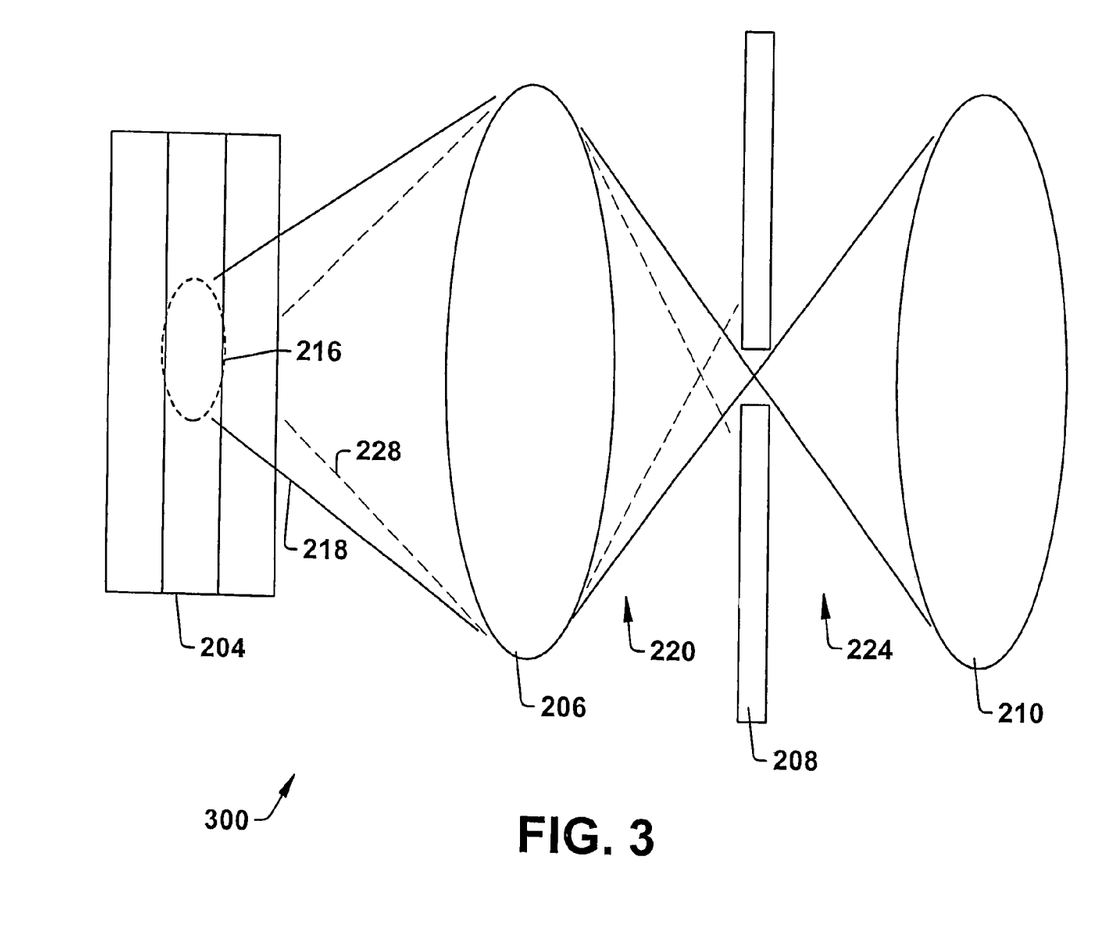
FIG. 3 is a diagram illustrating a portion 300 of the defect detection system of FIG. 2 in accordance with an aspect of the present invention.

FIG. 3 is a diagram illustrating a portion 300 of the defect detection system 200 of FIG. 2 in accordance with an aspect of the present invention. The diagram is presented in order to facilitate a better understanding of the present invention by illustrating other planes of x-ray energy that are blocked by the confocal plate 208.

As described above, the x-ray beam 214 from the x-ray source 202 passes through the semiconductor device 204. A portion of that energy passes through the target portion 216 of the device 204 and has been referred to as transmitted x-ray beam 218. This portion is specific to the selected depth of field and is limited to the selected layer and it is this energy that permits analyzing the target region 216 for defects. X-ray energy also passes through other portions of the device and is also transmitted. For example, x-ray beam 228 is depicted as resulting from a layer under the target portion 216. The present invention mitigates such undesired x-ray beams 228 from reaching the detectors 212.

It can be seen that the first focus component 206 bends the transmitted x-ray beam 218 toward a center of the confocal aperture 222. However, the other x-ray beam 228 is bent toward a different focal point and, as a result, impacts the confocal plate 208. Instead of passing through the aperture 222 as the focused x-ray beam 220 does, the other x-ray beam 228 is absorbed or blocked by the confocal plate 208.

As a result, the detectors 212 and the analysis component receive only x-ray energy that has passed or transmitted through the target portion 216 of the semiconductor device 204. Thus, more accurate analysis and defect detection can occur due to the reduced interference of x-rays carrying information from other planes in the semiconductor device 204.

Figure 4:
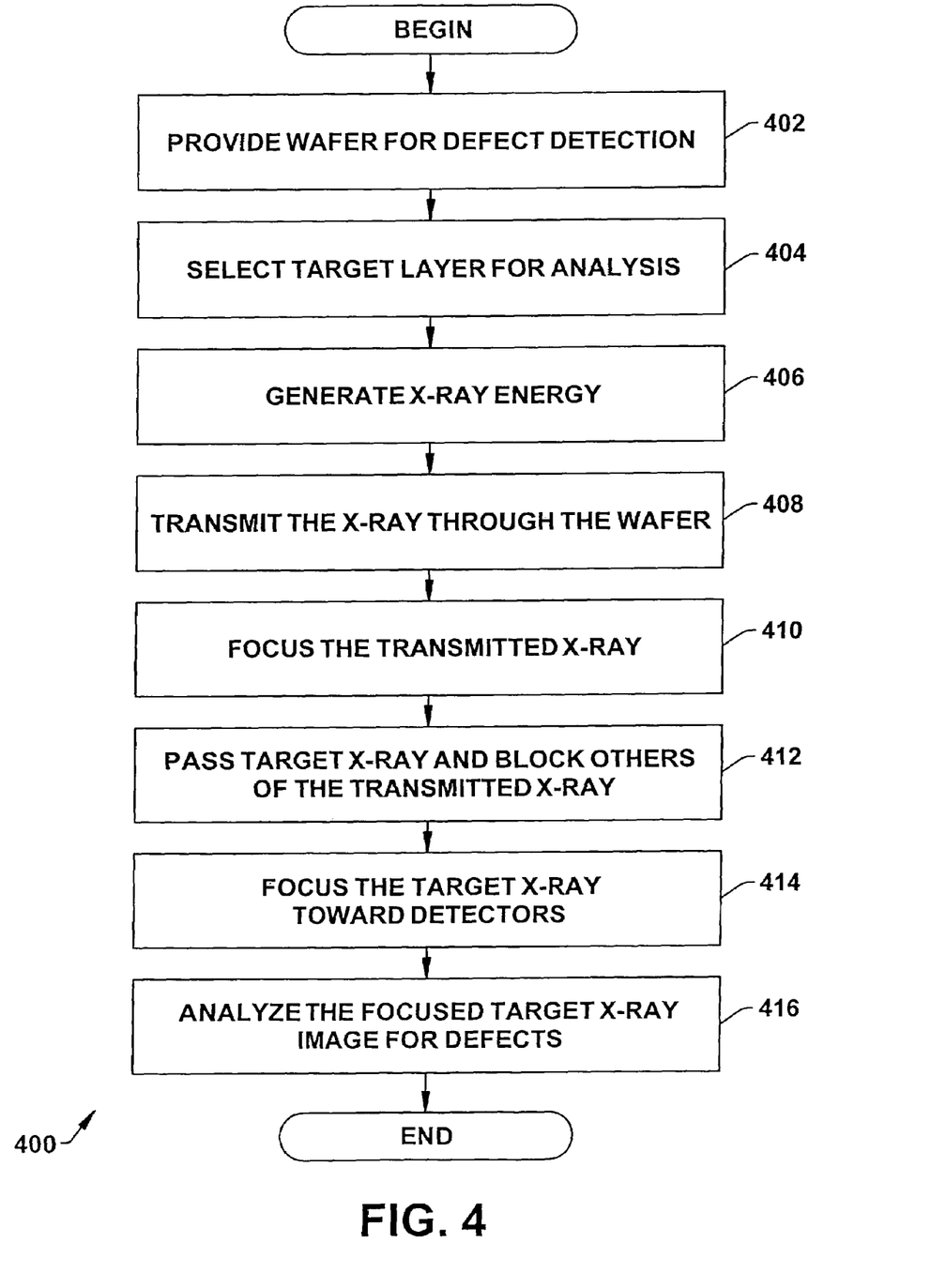
FIG. 4 is a flow diagram illustrating a method of using a confocal mechanism to identify and analyze defects in accordance with an aspect of the present invention.

FIG. 4 is a flow diagram illustrating a method 400 of using a confocal mechanism to identify and analyze defects in accordance with an aspect of the present invention. The method 400 employs the confocal mechanism to selectively limit and/or narrow a depth of field for transmitted x-ray energy such that only a selected or targeted portion of a device is analyzed and interference of x-rays carrying information from other portions is mitigated.

While, for purposes of simplicity of explanation, the method 400 is depicted and as executing serially, it is to be understood and appreciated that the present invention is not limited by the illustrated order, as some aspects could, in accordance with the present invention, occur in different orders and/or concurrently with other aspects from that depicted and described herein. Moreover, not all illustrated features may be required to implement a methodology in accordance with an aspect the present invention.

The method 400 begins at block 402 wherein a wafer, which includes semiconductor devices, is provided for defect detection. The wafer is comprised of a semiconductor material and is at a particular stage of fabrication. In one example, the wafer is at a stage of fabrication wherein a first copper layer is formed therein. In another example, the wafer is at a stage of fabrication wherein a plurality of metallization layers are formed.

The wafer is also positioned so as to be properly oriented with respect to an x-ray source. The wafer may be positioned with an underside of the substrate facing towards the x-ray source and a fabricated side comprising multiple layers facing away from the x-ray source.

A target layer or portion of the wafer is selected at block 404 for analysis. As an example, a third metallization layer of three metallization layers may be selected for analysis. A depth of field can also be selected that corresponds to or is related to the selected layer. It is noted that, in the chip fabrication sequence, the wafer can be inspected at several points in the flow, and the top-most metal level can be inspected for defects and/or voids without interference from the levels below. Alternately, a selected lower level and/or multiple levels and also be inspected.

X-ray energy is generated or produced at block 406 by an x-ray source and propagated toward the wafer. The x-ray source generates the x-ray energy with a particular energy and wavelength that is selected according to the target layer of the wafer.

The x-ray energy is transmitted or passed through the wafer at block 408. As noted previously, various materials within semiconductor devices absorb x-ray energy at different rates. As a result, some of the x-ray energy is absorbed by the various portions of the wafer. The x-ray energy is at least transmitted through the target layer or portion.

Subsequently, the transmitted x-ray energy is focused by a first focus mechanism at block 410. A portion of the transmitted x-ray energy, referred to as the target x-ray energy, is focused toward a confocal point, typically a center of a confocal aperture. As a result, other planes of the transmitted x-ray energy are focused away from the confocal point.

The first focus mechanism can employ, for example, a lens that uses refraction to bend or focus the transmitted x-ray energy. As another example, the first focus mechanism can employ a zone plate that uses diffraction to bend or focus the transmitted x-ray energy.

The other planes of the transmitted x-ray energy are blocked and the target x-ray energy is permitted to pass through or continue at block 412. Generally, a confocal plate containing the confocal aperture is employed to block the other planes of the transmitted x-ray energy. The confocal plate, if employed, absorbs the unwanted x-ray energy. The size or diameter of the confocal aperture limits or selects the depth of field, as stated as above. As a result, the confocal aperture is related to a size or depth of the target layer.

The target x-ray energy is again focused by a second focus mechanism at block 414 toward defect detectors. The second focus mechanism selectively bends or focuses the target x-ray energy such that it is focused about the defect detectors. It is noted that x-ray energy from other portions of the device has been blocked and, therefore, is not focused at block 414. The second focus mechanism can employ, for example, a lens that uses refraction to bend or focus the target x-ray energy or a zone plate that uses diffraction to bend or focus the target x-ray energy.

The target x-ray energy is received and analyzed for defects at block 416. Defect detectors, which comprise a plurality of x-ray detectors, receive the target x-ray energy. Digital images can then be formed from the received x-ray energy where variations in intensity and wavelength can indicate structural differences in the target layer. The digital images can be analyzed, for example by an analysis component, to identify defects from the digital images. In one example, an analysis component compares the formed digital images with expected or ideal images. Variations between the two are further analyzed in order to identify defects, such as copper voids, dielectric defects, and the like.

While the invention has been illustrated and described with respect to one or more implementations, alterations and/or modifications may be made to the illustrated examples without departing from the spirit and scope of the appended claims. In particular regard to the various functions performed by the above described components or structures (assemblies, devices, circuits, systems, etc.), the terms (including a reference to a "means") used to describe such components are intended to correspond, unless otherwise indicated, to any component or structure which performs the specified function of the described component (e.g., that is functionally equivalent), even though not structurally equivalent to the disclosed structure which performs the function in the herein illustrated exemplary implementations of the invention. In addition, while a particular feature of the invention may have been disclosed with respect to only one of several implementations, such feature may be combined with one or more other features of the other implementations as may be desired and advantageous for any given or particular application. Furthermore, to the extent that the terms "including", "includes", "having", "has", "with", or variants thereof are used in either the detailed description and the claims, such terms are intended to be inclusive in a manner similar to the term "comprising".

What is claimed is:

1. An x-ray confocal defect detection system comprising:
   an x-ray source that generates initial x-ray energy;
   a semiconductor device through which the initial x-ray energy transmits as transmitted x-ray energy, wherein the semiconductor device includes a target portion;
   a confocal component that passes target x-ray energy transmitted through the target portion and removes other x-ray energy comprising:
      a first focus mechanism that receives the transmitted energy including the target x-ray energy from the target portion and focuses only the target x-ray energy toward a confocal focal point; and
      a second focus mechanism positioned downstream of the first focus mechanism that receives the target x-ray energy and focuses the target x-ray energy toward the detectors; and
   detectors that receive the target x-ray energy from the target portion of the semiconductor device.

2. The system of claim 1, wherein the initial x-ray energy has a selected intensity and wavelength according to the semiconductor device and the target portion.

3. The system of claim 1, wherein the initial x-ray energy is collimated x-ray energy.

4. The system of claim 1, wherein the semiconductor device absorbs a portion of the transmitted x-ray energy.

5. The system of claim 1, wherein the confocal component further comprises:
   a confocal plate positioned downstream of the first focus mechanism and upstream of the second focus mechanism comprising a confocal aperture centered about the confocal focal point, wherein the confocal plate absorbs other portions of the transmitted x-ray energy and the confocal aperture permits passage of the target x-ray energy.

6. The system of claim 5, wherein the first focus mechanism comprises an x-ray lens.

7. The system of claim 5, wherein the first focus mechanism comprises a zone plate and the second focus mechanism comprises a zone plate.

8. The system of claim 5, wherein the confocal aperture has a diameter according to a depth of field for the target portion of the semiconductor device.

9. The system of claim 1, wherein the detectors comprise a plurality of x-ray detectors.

10. The system of claim 1, wherein the detectors generate a signal according to the intensity and position of the target x-ray energy.

11. The system of claim 10, further comprising an analysis component that employs the signal from the detectors to form an x-ray image of the target portion of the semiconductor device.

12. The system of claim 11, wherein the analysis component compares the x-ray image with an expected image and identifies defects within the target portion.

13. The system of claim 12, wherein the defects include copper voids and/or voids within dielectric layers.

14. The system of claim 11, wherein the analysis component compares the x-ray image with previous images of same relative locations in a plurality of nearest neighbor dies.

15. The system of claim 11, wherein the analysis component compares the x-ray image with previous images of same relative locations in a plurality of neighboring cells.

16. The system of claim 1, wherein the semiconductor device comprises a first metallization layer, a second metallization layer formed on the first metallization layer, and a third metallization layer formed on the second metallization layer and wherein the target portion includes only the second metallization layer.

17. A confocal component comprising:
   a first focus mechanism that receives transmitted x-ray energy from a semiconductor device and focuses a portion of the x-ray energy from a target portion of the semiconductor device toward a confocal focal point;
   a confocal plate positioned downstream of the first focus mechanism comprising a confocal aperture centered about the confocal focal point, wherein the confocal plate absorbs other portions of the transmitted x-ray energy and the confocal aperture permits passage of the portion of the x-ray energy from the target portion; and
   a second focus mechanism that receives the portion of the x-ray energy from the target portion and focuses the portion of the x-ray energy from the target portion at a second focal point.

18. The component of claim 17, wherein the first focus mechanism comprises a zone plate and the second focus mechanism comprises an x-ray lens.

19. The confocal component of claim 17, further comprising an x-ray source that generates the transmitted x-ray energy and x-ray detectors that receive only the portion of the x-ray energy from the target portion.

20. A method of performing defect detection comprising:
   providing a wafer having a plurality of formed layers thereon;
   selecting a target layer of the plurality of formed layers for defect analysis;
   generating x-ray energy having a selected intensity and wavelength toward the wafer;
   transmitting the x-ray energy through the wafer wherein portions of the x-ray energy are absorbed by various portions of the wafer at various absorption rates;
   focusing a target portion of the transmitted x-ray energy from the target layer toward a first focal point;

blocking other portions of the transmitted x-ray energy from other portions of the wafer and permitting passage of the target portion of the transmitted x-ray energy; and focusing only the target portion toward a second focal point.

21. The method of claim 20, further comprising generating x-ray images of the target layer from the target x-ray energy at the second focal point.

22. The method of claim 21, further comprising identifying defects from the generated x-ray images.

23. The method of claim 20, wherein selecting the target layer comprises selecting a first metallization layer.

24. The method of claim 20, wherein focusing a target portion of the transmitted x-ray energy further comprises focusing other portions of the transmitted x-ray energy away from the first focal point.

* * * * *